United States Patent
Budhabhatti et al.

(10) Patent No.: US 10,251,652 B2
(45) Date of Patent: Apr. 9, 2019

(54) FEMORAL AND TIBIAL CUTTING BLOCKS

(71) Applicant: Smith & Nephew, Inc., Memphis, TN (US)

(72) Inventors: Sachin P. Budhabhatti, Collierville, TN (US); Ravi Bagathur Ramasamy, Collierville, TN (US); Tom J. Francis, Cordova, TN (US)

(73) Assignee: Smith & Nephew, Inc., Memphis, TN (US)

( * ) Notice: Subject to any disclaimer, the term of this patent is extended or adjusted under 35 U.S.C. 154(b) by 162 days.

(21) Appl. No.: 15/118,005

(22) PCT Filed: Feb. 11, 2015

(86) PCT No.: PCT/US2015/015376
§ 371 (c)(1),
(2) Date: Aug. 10, 2016

(87) PCT Pub. No.: WO2015/123270
PCT Pub. Date: Aug. 20, 2015

(65) Prior Publication Data
US 2017/0014139 A1    Jan. 19, 2017

Related U.S. Application Data

(60) Provisional application No. 61/938,520, filed on Feb. 11, 2014, provisional application No. 62/083,009, filed on Nov. 21, 2014.

(51) Int. Cl.
*A61B 17/15* (2006.01)
*A61B 90/00* (2016.01)

(52) U.S. Cl.
CPC .......... *A61B 17/154* (2013.01); *A61B 17/155* (2013.01); *A61B 17/157* (2013.01); *A61B 90/06* (2016.02); *A61B 2090/067* (2016.02)

(58) Field of Classification Search
CPC ..... A61B 17/15; A61B 17/154; A61B 17/155; A61B 17/157; A61B 90/00; A61B 90/06
See application file for complete search history.

(56) References Cited

U.S. PATENT DOCUMENTS

| 5,662,656 A * | 9/1997 | White | A61B 17/155 |
| | | | 606/86 R |
| 7,029,477 B2 * | 4/2006 | Grimm | A61B 17/157 |
| | | | 606/88 |

(Continued)

FOREIGN PATENT DOCUMENTS

| CN | 103237510 A | 8/2013 |
| EP | 1559375 A1 | 8/2005 |

(Continued)

OTHER PUBLICATIONS

International Search Report; European Patent Office; International Application No. PCT/US2015/015376; dated Apr. 14, 2015; 5 pages.

(Continued)

*Primary Examiner* — Christopher Beccia
(74) *Attorney, Agent, or Firm* — Taft Stettinius & Hollister LLP

(57) ABSTRACT

Embodiments of the invention include a cutting block and methods for guiding the cutting of a tibia and a femur in preparation for one or more knee arthroplasty implants. Some embodiments include configurations and methods that enable a common cutting block positioned medially, laterally, or centrally relative to a tibia, and to be positioned relative to a femur on either of a patient's left leg or right leg.

33 Claims, 9 Drawing Sheets

(56) References Cited

U.S. PATENT DOCUMENTS

| | | | |
|---|---|---|---|
| 2006/0155294 A1 | 7/2006 | Steffensmeier et al. | |
| 2007/0186738 A1* | 8/2007 | McGinley | A61B 17/157 83/88 |
| 2008/0015602 A1 | 1/2008 | Axelson | |
| 2010/0318089 A1* | 12/2010 | Metzger | A61B 17/155 606/88 |

FOREIGN PATENT DOCUMENTS

| | | |
|---|---|---|
| EP | 2092899 A2 | 8/2009 |
| WO | 2004008988 A2 | 2/2004 |
| WO | 2012176077 A1 | 12/2012 |

OTHER PUBLICATIONS

Written Opinion of the International Searching Authority; European Patent Office; International Application No. PCT/US2015/015376; dated Apr. 14, 2015; 7 pages.
European Examination Report; European Patent Office; European Patent Application No. 15706993.1; dated Oct. 22, 2018; 3 pages.
Chinese Search Report; State Intellectual Property Office, Peoples Republic of China; Chinese Patent Application No. 201580019282.2; dated May 24, 2018; 5 pages.
Chinese Office Action (1st); State Intellectual Property Office, Peoples Republic of China; Chinese Patent Application No. 201580019282.2; dated Jun. 4, 2018; 20 pages.

* cited by examiner

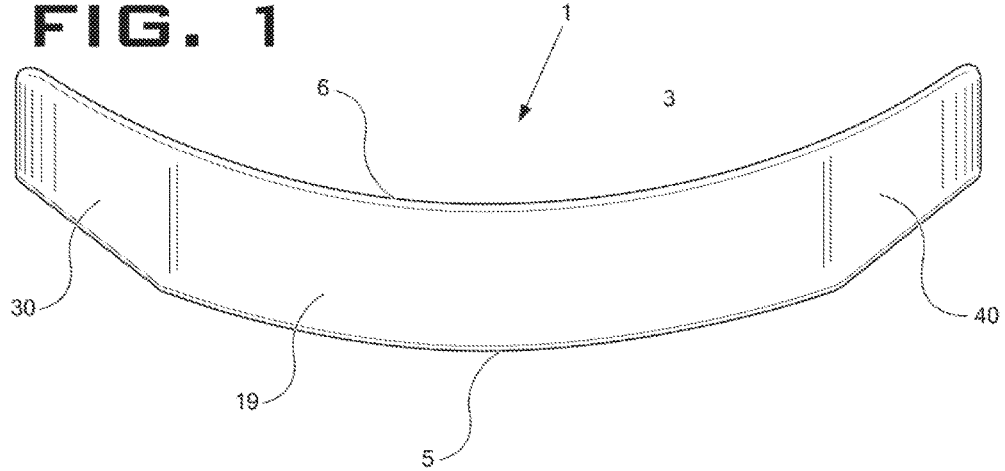
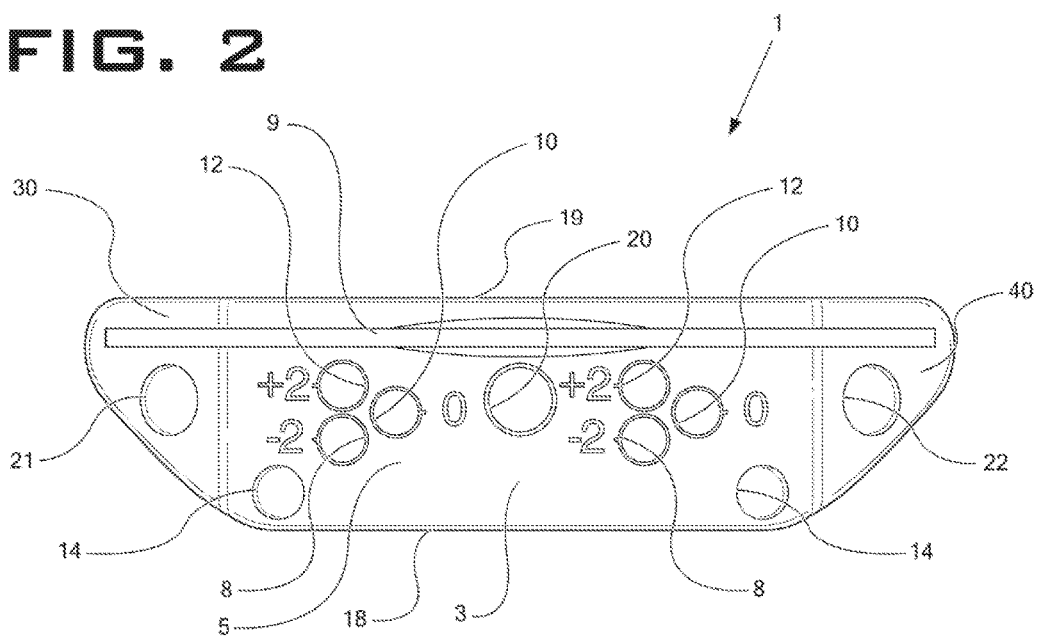

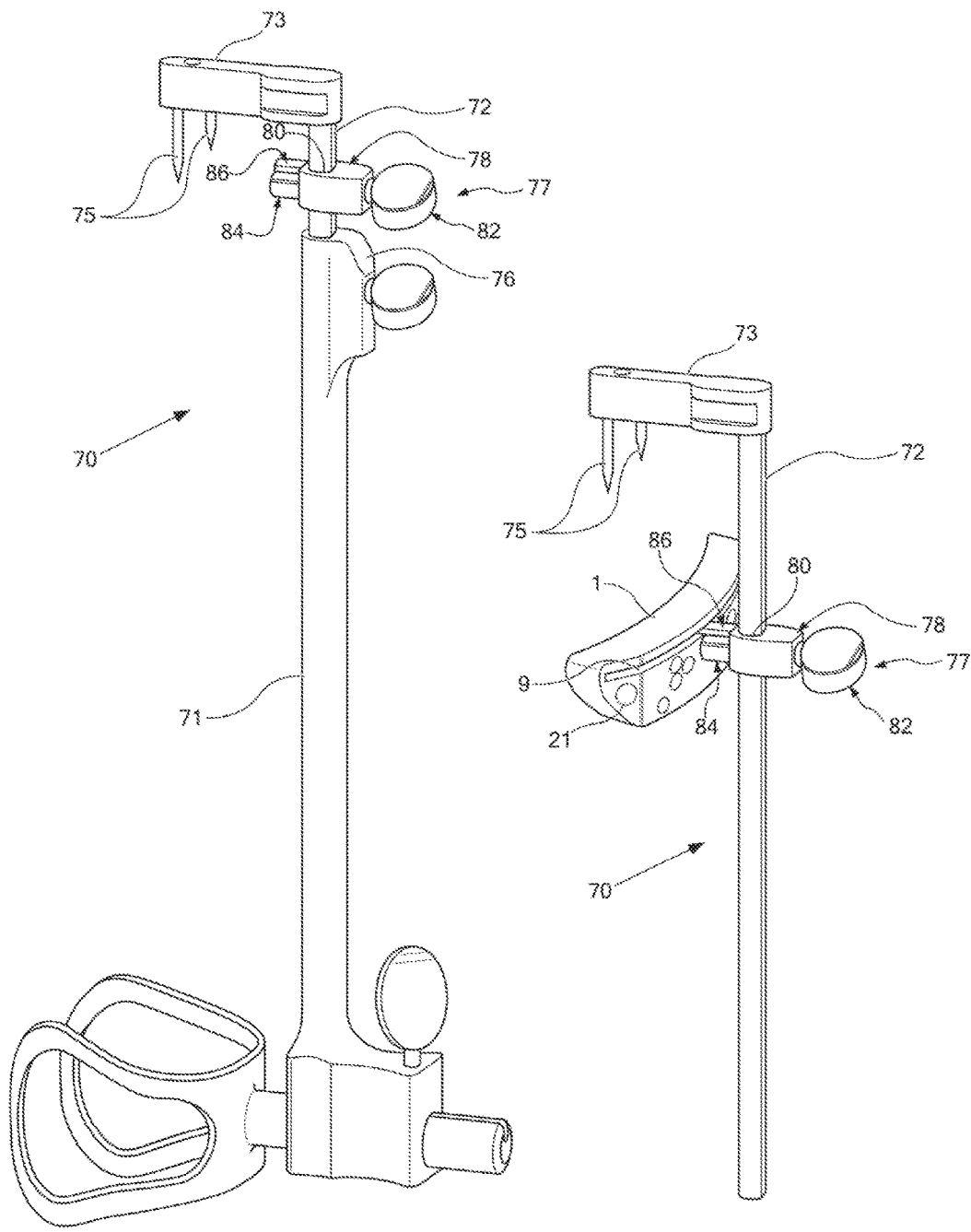

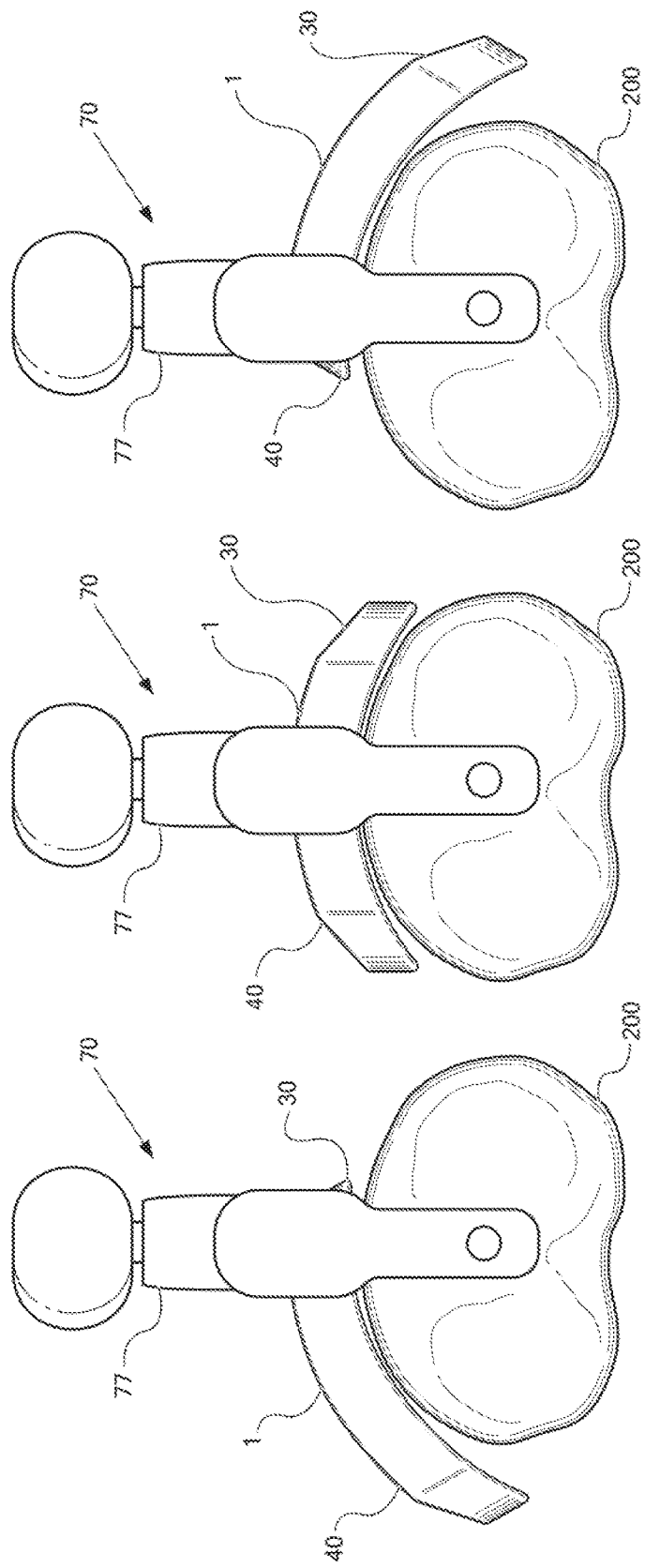

FEMORAL AND TIBIAL CUTTING BLOCKS

CROSS REFERENCE TO RELATED APPLICATIONS

This application is a U.S. National Phase of International PCT Application No. PCT/US2015/015376 filed Feb. 11, 2015, which claims the benefit of U.S. Provisional Application No. 61/938,520 filed Feb. 11, 2014 and U.S. Provisional Application No. 62/083,009 filed Nov. 21, 2014, the contents of each application hereby incorporated by reference in its entirety.

FIELD OF THE INVENTION

The present invention relates generally to the field of medical instruments and device, and more particularly, but not exclusively, relates to one or more cutting blocks and methods that may be used both to prepare a tibia and a femur to receive knee arthroplasty implants.

BACKGROUND

Knee arthroplasty procedures generally require resection or cutting of both a femur at its distal end and a tibia at its proximal end. These resections or cuts are conventionally accomplished with the aid of a set of cutting blocks that guide and direct cutting at a desired location and orientation. Current knee arthroplasty systems typically require several different cutting blocks to guide and direct the cutting of the distal femur and proximal tibia of both of a patient's right and left legs. Some knee arthroplasty systems require additional sets of instruments to accommodate different sizes and different orientations, angles and adjustments. Consequently, some knee arthroplasty systems configured to provide cutting blocks to meet each of these design requirements include a significant number of cutting blocks. Even some systems that include cutting blocks used for more than one of these purposes could be improved by meeting more of the purposes and requirements via a smaller number of cutting blocks.

Distal femoral and proximal tibial cutting blocks can add significantly to the overall number of instruments included in a knee arthroplasty system instrument set. Large instrument sets are expensive to manufacture, expensive to ship, cumbersome to handle, time and cost intensive to clean and sterilize, and may be more complicated to learn how to effectively use. A single cutting block or a reduced number of cutting blocks and related techniques that are capable of providing guidance and direction of cutting of both the distal femur and proximal tibia of either of a patient's right leg or left leg could therefore reduce costs and improve overall efficiency.

SUMMARY

An embodiment of the invention includes a cutting block configured to guide cutting of a tibia and a femur in preparation for one or more knee arthroplasty implants. The cutting block may have a body that includes a front, a back, and one or more holes through which fasteners may be coupled with the tibia or the femur, a first wing adjacent to the body, and a second wing adjacent to the body and positioned opposite the first wing. In some embodiments, the body, the first wing, and the second wing include substantially similar openings configured to couple with a tibial alignment instrument such that the cutting block may be coupled with the tibial alignment instrument to position the cutting block medially, laterally, or centrally relative to the tibia. A second embodiment of a cutting block is configured to guide cutting of both a tibia and a femur.

Another embodiment of the invention includes an instrument set configured to guide cutting of a tibia and a femur in preparation for one or more knee arthroplasty implants. Instrument set embodiments may include a femoral alignment instrument, a tibial alignment instrument, and a cutting block configured to couple with the femoral alignment instrument and the tibial alignment instrument. The cutting block may have a body that includes a front, a back, and one or more holes through which fasteners may be coupled with the tibia or the femur. The cutting block may also have a first wing adjacent to the body and a second wing adjacent to the body and positioned opposite the first wing. In some embodiments, the body, the first wing, and the second wing include substantially similar openings configured to couple with the tibial alignment instrument such that the cutting block may be coupled with the tibial alignment instrument to position the cutting block medially, laterally, or centrally relative to the tibia. The opening in the body configured to couple with the tibial alignment instrument may also be configured to couple with the femoral alignment instrument.

Another embodiment of the invention includes an instrument set having cut block slide connector configured to be attached to the tibial instrument set such that the cutting block may be moved either medially or laterally with respect to the tibia to allow for proper positioning of the cutting block with respect to the tibia.

Yet another embodiment of the invention includes a method of preparing a tibia and a femur to receive one or more knee arthroplasty implants. Method embodiments may include providing a cutting block configured to guide cutting of a distal femur and to guide cutting of a proximal tibia, aligning a femoral alignment instrument with the femur to enable a distal cut of the femur, coupling the cutting block to the femoral alignment instrument, and making the distal cut of the femur. Method embodiments may also include aligning a tibial alignment instrument with the tibia to enable a proximal cut of the tibia, coupling the cutting block to the tibial alignment instrument at one of three different openings in the cutting block wherein the three different openings are substantially similar openings configured to couple with the tibial alignment instrument such that the cutting block may be coupled with the tibial alignment instrument to position the cutting block medially, laterally, or centrally relative to the tibia, and making the proximal cut of the tibia.

BRIEF DESCRIPTION OF THE DRAWINGS

FIG. 1 is a top plan view of a cutting block according to one embodiment.

FIG. 2 is a front elevation view of the cutting block of FIG. 1.

FIG. 7 is a perspective view of a tibial alignment instrument according to one embodiment.

FIG. 8 is a perspective view of a portion of the tibial alignment instrument of FIG. 7 coupled with the cutting block of FIGS. 1-6.

FIG. 9 is a top plan view of the tibial alignment instrument and cutting block of FIG. 8 with the cutting block positioned laterally relative to the tibia.

FIG. 10 is a top plan view of the tibial alignment instrument and cutting block of FIG. 8 with the cutting block positioned centrally relative to the tibia.

FIG. 11 is a top plan view of the tibial alignment instrument and cutting block of FIG. 8 with the cutting block positioned medially relative to the tibia.

DETAILED DESCRIPTION

One embodiment of a cutting block 1 is illustrated in two views in FIGS. 1 and 2. The cutting block 1 is configured to guide the cutting of a tibia and a femur in preparation for one or more knee arthroplasty implants. The cutting block 1 includes a body 3 with a front 5 and a back 6. The illustrated cutting block 1 is generally curved along its entire length. Although portions of the cutting block 1 are not specifically illustrated as being curved, as used herein, such an overall shape is considered generally curved. As illustrated in FIG. 1, a generally convex side of the curve in the cutting block 1 includes the front 5 of the body 3, and a generally concave side of the curve in the cutting block 1 includes the back 6 of the body 3. In the illustrated embodiment, the body 3 is also generally curved. The curve of the body 3 is such that the generally convex side of the body 3 is on the front 5 of the body 3, and the generally concave side is on the back 6 of the body 3. However, other embodiments are also contemplated.

Figure 5:
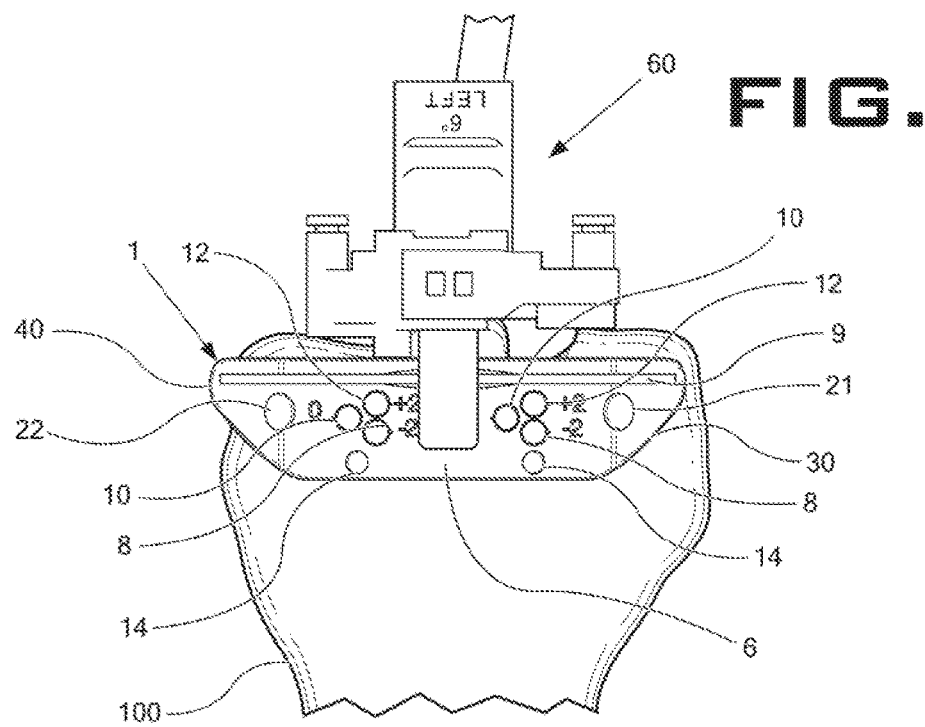
FIG. 5 is a front elevation view of the cutting block and femoral alignment instrument of FIG. 3.

As shown in FIGS. 2 and 5, multiple holes extend through the body 3 of the cutting block 1, through which extend fasteners that may be coupled with a tibia or a femur. Specifically, the body 3 includes base holes 10, negative adjustment holes 8, positive adjustment holes 12, and skewed holes 14. A body opening 20 is also illustrated in the central portion of the body 3. In the illustrated embodiment, the base holes 10, the negative adjustment holes 8, and the positive adjustment holes 12 extend along axes that are arranged generally parallel with one another. The parallel axes of the base holes 10, the negative adjustment holes 8, and the positive adjustment holes 12 enable the holes to be used to incrementally adjust the position of the cutting block 1 relative to a tibia or a femur without repositioning fasteners that have been coupled to the tibia or the femur. Note that the medial to lateral distance between the base holes 10, the negative adjustment holes 8, and the positive adjustment holes 12 is generally the same. Consequently, in instances where fasteners have been placed in a tibia or a femur such that the fasteners align with the base holes 10, the cutting block 1 may be slid over the fasteners and adjusted distally or proximally by placing the cutting block 1 over the negative adjustment holes 8 or the positive adjustment holes 12, respectively. Such an adjustment displaces the cutting block 1 slightly medially or slightly laterally, but this displacement does not interfere with a surgeon's ability to accurately complete a resection with the cutting block 1.

As illustrated in FIG. 2, the front 5 of the body 3 includes markings (0, +2, −2) that are used to indicate relative adjustments which may be made to a position of the cutting block 1 relative to a tibia or a femur by removing the cutting block 1 from one or more fasteners positioned in a set of one or more holes in the cutting block 1, and placing the cutting block 1 over the one or more fasteners in a different set of the one or more holes in the cutting block 1. As illustrated in FIG. 5, the back 6 of the body 3 also includes similar markings (0, +2, −2) that are used to indicate relative adjustments which may be made to a position of the cutting block 1 relative to a tibia or a femur by removing the cutting block 1 from one or more fasteners positioned in a set of one or more holes in the cutting block 1, and placing the cutting block 1 over the one or more listeners in a different set of the one or more holes in the cutting block 1. The illustrated cutting block 1 also includes skewed holes 14 extending along axes that are not arranged parallel with one another. In addition to not having axes arranged parallel with one another, the skewed holes 14 also have axes that are not arranged parallel with the axes of the base holes 10, the negative adjustment holes 8, and/or the positive adjustment holes 12. The non-parallel axes of the holes may provide an advantage in some embodiments of more positively coupling the cutting block 1 to a femur or a tibia in view of the fact that nonparallel axes prevent sliding of the cutting block 1 in a common direction along two or more fasteners placed in nonparallel holes.

A first wing 30 of the cutting block 1 is illustrated in FIGS. 1 and 2 as being positioned adjacent to the body 3. A second wing 40 is also illustrated as being positioned adjacent to the body 3 and positioned opposite from the first wing 30. The illustrated first wing 30 includes an opening configured to couple with a tibial alignment instrument. Considering the body 3 to have a major axis that primarily extends in a medial to lateral direction along the greater length or longitudinal dimension of the body 3, and considering the first wing 30 to have a major axis that is primarily arranged along the greater length or longitudinal dimension of the first wing 30 (as illustrated in FIG. 1), the first wing 30 has a major axis that is not parallel with a major axis of the body 3. Again considering the body 3 to have a major axis that primarily extends in a medial to lateral direction along the greater length or longitudinal dimension of the body 3, and considering the second wing 40 to have a major axis that is arranged primarily along the greater length or longitudinal dimension of the second wing 40 (as illustrated in FIG. 1), the second wing 40 has a major axis that is not arranged parallel with a major axis of the body 3. In other embodiments, the first wing 30 and the second wing 40 may have major axes, with one or both of the major axes arranged coaxial and parallel with the major axis of the body 3 and with one another.

In FIGS. 2 and 5, a first wing opening 21 is illustrated in the first wing 30, and a second wing opening 22 is illustrated in the second wing 40. The first wing opening 21 and the second wing opening 22 are substantially sized and shaped similar to the body opening 20 in the illustrated embodiment. Each of the openings 20, 21, 22 in the illustrated embodiment have the same general size and shape. Sized and shaped openings of any operative type may be used with the illustrated embodiment or with other embodiments. Openings in other embodiments may have a smooth interior surface, may be threaded, or may include other features that assist with coupling instruments with the openings.

Figure 3:
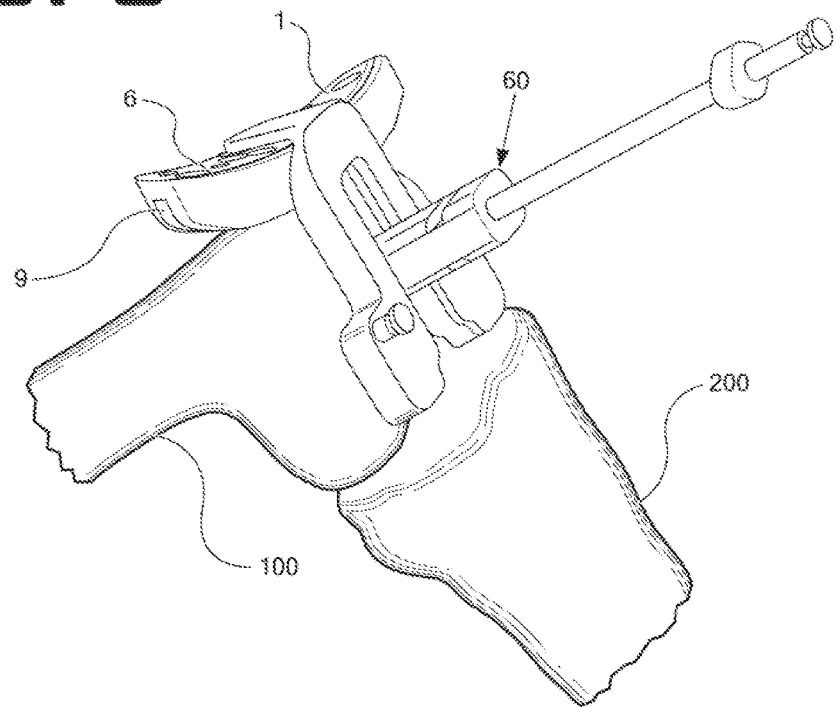
FIG. 3 is a perspective view of the cutting block of FIG. 1 coupled to a femoral alignment instrument.
Figure 4:
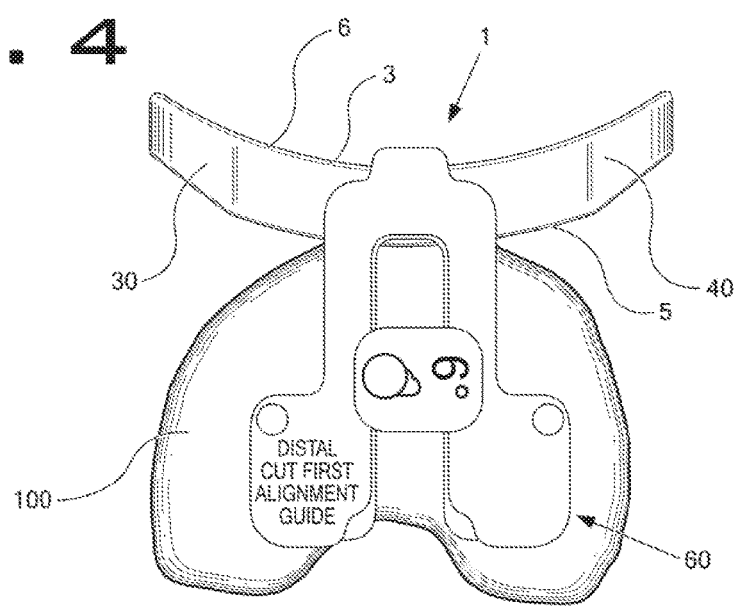
FIG. 4 is a top plan view of the cutting block and femoral alignment instrument of FIG. 3.

A femoral alignment instrument 60 illustrated in FIGS. 3-5 is coupled with the body opening 20 in the body 3. In FIGS. 8 and 10, a tibial alignment instrument 70 is coupled with the body opening 20 in the body 3. With the tibial alignment instrument 70 coupled with the body opening 20 (as shown in FIGS. 8 and 10), the cutting block 1 is correspondingly positioned centrally relative to the tibia 200 (FIG. 10). With the tibial alignment instrument 70 coupled with the first wing opening 21 in the first wing 30, the cutting block 1 is correspondingly positioned laterally relative to the tibia 200 (FIG. 9). With the tibial alignment instrument 70 coupled with the second wing opening 22 in the second wing 40, the cutting block 1 is correspondingly positioned medially relative to the tibia 200 (FIG. 11). Therefore, in the illustrated embodiment, the cutting block 1 may be coupled with the tibial alignment instrument 70 to position the cutting block 1 medially, laterally or centrally relative to the tibia 200. Additionally, in the illustrated embodiment, the body opening 20, the first wing opening 21, and the second wing opening 22 have converging axes. As a result, coupling of the cutting block 1 with the tibial alignment instrument 70 via the openings while maintaining the tibial alignment instrument 70 in a constant position relative to the tibia 200 correspondingly rotates the cutting block 1 relative to the tibia 200. This effect is more specifically illustrated in FIGS. 9-11.

The illustrated embodiment of the cutting block 1 also includes a longitudinal slot 9, as shown in FIGS. 2, 3, 5, 8 and 12. The longitudinal slot 9 is useful in guiding and directing a cutting instrument 90 used to cut a femur or a tibia, as shown, for example, in FIGS. 6 and 12. A slot, guide or opening of any other effective shape may be used in other embodiments. In some embodiments, a top surface 19 (FIGS. 1 and 2) or a bottom surface 18 (FIG. 2) of the cutting block 1 could also be used to guide the cutting of a tibia or a femur.

One embodiment of the invention includes an instrument set configured to guide cutting of a tibia and a femur in preparation for one or more knee arthroplasty implants. The instrument set embodiments may include, for example, a femoral alignment instrument such as the femoral alignment instrument 60 illustrated in FIGS. 3-5, and/or a tibial alignment instrument such as the tibial alignment instrument 70 illustrated in FIGS. 7-11. The femoral alignment instrument 60 includes an intramedullary portion configured to be inserted into the intramedullary canal of the femur 100. The illustrated embodiment of the femoral alignment instrument 60 is capable of angular adjustment to aid the surgeon in achieving a desired alignment relative to the femur 100 and/or other skeletal anatomy of the patient. However, some embodiments need not necessarily include any adjustments mechanisms, but may be rely solely on the angle of the intramedullary canal for alignment. Other embodiments of femoral alignment instruments need not necessarily depend in any way on the intramedullary canal of a femur, but may instead be extramedullary and fixed by some other mechanism to the femur or another anatomic reference to achieve desired alignment.

The tibial alignment instrument 70 illustrated in FIGS. 7-11 is an extramedullary device, and the illustrated embodiment does not include an intramedullary portion configured to be inserted in the intramedullary canal of the tibia 200. However, in other embodiments, a tibial alignment instrument may be provided which includes an intramedullary device to assist with alignment of the instrument relative to the tibia 200. It should be understood that other types of tibial alignment instruments now known or later conceived that cooperate with the other features described herein are contemplated as falling within the scope of embodiments of the present invention. The illustrated embodiment of the tibial alignment instrument 70 includes a distal portion 71 and a proximal portion 72. The proximal portion 72 includes a head 73 with spikes 75 extending therefrom which are configured to engage a proximal end of the tibia 200 (FIGS. 9-11). The tibial alignment instrument 70 is configured to telescopically adjust in a longitudinal direction by sliding of the proximal portion 72 within the distal portion 71. A lock mechanism 76 is provided to fix the length or longitudinal dimension of the tibial alignment instrument 70 when a desired length is achieved. A cutting block holder 77 configured to engage the body opening 20 and the longitudinal slot 9 of the cutting block 1 is illustrated in FIGS. 7-11. The cutting block holder 77 is configured to slide along the proximal portion 72 of the tibial alignment instrument 70. The illustrated cutting block holder 77 is capable of being locked at a desired location when alignment of the cutting block 1 relative to the tibia 200 is achieved.

As illustrated in FIGS. 3-5 and 8-11, the cutting block 1 is capable of coupling with the femoral alignment instrument 60 and/or the tibial alignment instrument 70. The cutting block of various instrument set embodiments may be, but is not necessarily, configured the same as or similar to the cutting block 1 and variations to the cutting block 1 described in detail herein.

An embodiment of the invention includes a method of preparing a tibia in a femur to receive one or more knee arthroplasty implants. Method embodiments may include providing a cutting block configured to guide cutting of a distal femur and to guide cutting of a proximal tibia. For example and without limitation, the cutting block 1 illustrated in FIGS. 1-6 and 8-12 may be provided with some methods. A method embodiment includes aligning a femoral alignment instrument, such as the femoral alignment instrument 60 illustrated in FIGS. 3-5, with the femur 100 to enable a distal cut of the femur 100. The cutting block 1 is shown coupled to the femoral alignment instrument 60 in FIGS. 3-5. This coupling may be accomplished prior to or after alignment of the femoral alignment instrument 60 with the femur 100 in various embodiments. In the illustrated embodiment, the femoral alignment instrument 60 includes a member that is inserted into the body opening 20 of the cutting block 1 to provide a coupling or attachment. However, any other suitable and effective mechanism may be utilized to accomplish a coupling or attachment between the cutting block 1 and the femoral alignment instrument 60. As illustrated in FIGS. 3-6, a front 5 of the body 3 of the cutting block 1 is directed toward the femur 100. In other embodiments, a back or other portion of a cutting block may be directed toward a femur designated to be cut.

In some embodiments, a cutting block may be coupled to a femur with one or more fasteners prior to the distal cutting of the femur. For example, in the illustrated embodiment shown in FIG. 6, fasteners 50 have been placed through holes in the cutting block 1 to couple the cutting block 1 to the femur 100. The fasteners 50 may be placed through any combination of the base holes 10, the negative adjustment holes 8, the positive adjustment holes 12, and the skewed holes 14. In some embodiments, the fasteners 50 may be headless or smooth fasteners initially/provisionally placed through the base holes 10. If an adjustment in a distal or proximal direction is necessary, the cutting block 1 may be removed from the fasteners and adjusted distally or proximally by placing the cutting block 1 over the negative adjustment holes 8 or the positive adjustment holes 12. Fasteners may also be placed through the skewed holes 14 to achieve coupling between the cutting block 1 and the femur 100 when no additional adjustment is anticipated, or if the surgeon is willing to remove fasteners to accomplish further adjustments.

Figure 6:
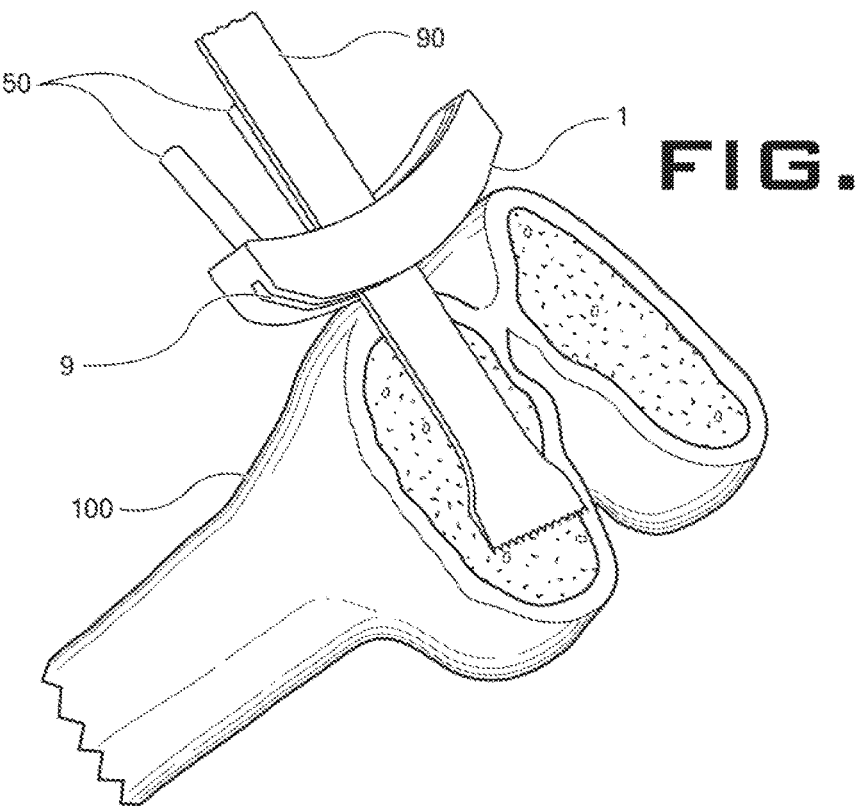
FIG. 6 is a perspective view of the cutting block of FIGS. 1-5 and a cutting instrument that is used to make a distal femoral cut.

Method embodiments may also include making a distal cut to a femur. For example and without limitation, a distal cut is shown in FIG. 6 which is formed via an end-saw 90 passing through the slot 9 in the cutting block 1. However, other suitable and effective types of saws, blades, burrs, or other cutting devices may be used to accomplish cutting of a distal femur.

Embodiments of the invention may also include aligning a tibial alignment instrument, such as but not limited to the tibial alignment instrument 70, with a tibia to enable formation of a proximal cut of the tibia. In FIGS. 8-11, the cutting block 1 is shown selectively coupled to the tibial alignment instrument 70. This selective coupling may be accomplished prior to or after alignment of the tibial alignment instrument 70 with the tibia 200.

In the illustrated embodiment, the tibial alignment instrument 70 includes a sliding cutting block holder 77 configured to engage the cutting block 1 via the longitudinal slot 9 and any of the central body opening 20, the first wing opening 21, and the second wing opening 22. (FIGS. 8-11). The cutting block holder 77 is generally provided with a body 78 that is provided with an aperture 80 which slidably receives the proximal portion 72 of the tibial alignment instrument 70 to permit adjustment of the axial position of the cutting block holder 77 along the proximal portion 72. The cutting block holder 77 also includes a thumb screw or fastener 82 having a shank extending through an opening in the body 78 and into engagement with the proximal portion 72 to allow the cutting block holder 77 to be affixed in a select position along and about the proximal portion 72.

In the illustrated embodiment, the cutting block holder 77 is provided with a pin 84 extending from the body 78 and sized and shaped for insertion into a select one of the central body opening 20 (FIGS. 8 and 10), the first wing opening 21 (FIG. 9), and the second wing opening 22 (FIG. 11) in the cutting block 1 to selectively engage or couple the cutting block holder 77 to the cutting block 1, which in turn selectively couples the tibial alignment instrument 70 with the cutting block 1. In the illustrated embodiment, the three openings 20, 21, 22 in the cutting block 1 are sized and shaped as substantially similar openings, and each is configured to couple with the tibial alignment instrument 70, and more specifically with the pin 84 of the cutting block holder 77, with the holder 77 in turn engaged with the proximal portion 72 of the tibial alignment instrument 70. By this configuration, the cutting block 1 may be selectively coupled with the tibial alignment instrument 70 to position the cutting block 1 medially (FIG. 11), laterally (FIG. 9), or centrally (FIG. 10) relative to the tibia 200. In other embodiments, alternative placements of openings and resultant positionings are contemplated. Additionally, any other suitable and effective mechanism may be utilized to accomplish a coupling or attachment between the cutting block 1 and the tibial alignment instrument 70. As illustrated in FIGS. 9-11, a back 6 of the body 3 of the cutting block 1 may be directed toward the tibia 200. However, in other embodiments, a front or other portion of the cutting block 1 may be directed toward the tibia 200 designated to be cut.

In the illustrated embodiment, the cutting block holder 77 is also provided with a generally flat tab 86 extending from the body 78 and positioned proximately adjacent the pin 84. In one embodiment, the tab 86 extends in a direction generally parallel to that of the pin 84. However, other embodiments are also contemplated where the tab 86 and the pin 84 are not arranged parallel with one another. The tab 86 is sized and shaped for receipt within the longitudinal cutting slot 9 of the cutting block 1 to further stabilize the cutting block holder 77 (and the tibial alignment instrument 70) relative to the cutting block 1, the details of which are discussed below.

In FIGS. 8-11, the cutting block 1 is shown selectively coupled to the tibial alignment instrument 70. More specifically, in FIGS. 8 and 10, the tibial alignment instrument 70 is shown with the pin 84 of the cutting block holder 77 inserted into the central body opening 20 of the cutting block 1 to accomplish central coupling of the tibial alignment instrument 70 with respect to the cutting block 1, and with the tab 86 inserted into the longitudinal slot 9 of the cutting block 1 to provide additional stabilization between the tibial alignment instrument 70 and the cutting block 1. Before the thumb screw 82 is fully tightened, the cutting block holder 77 is allowed to slide along and about the proximal portion 72 of the tibial alignment instrument 70 to adjust the position of the cutting block 1 with respect to the alignment instrument 70 and the tibia 200. In FIG. 9, the tibial alignment instrument 70 is shown with the pin 84 of the cutting block holder 77 inserted into the first wing opening 21 of the cutting block 1 to accomplish lateral coupling of the tibial alignment instrument 70 with respect to the cutting block 1, and with the tab 86 inserted into the longitudinal slot 9 of the cutting block 1 to provide additional stabilization between the tibial alignment instrument 70 and the cutting block 1. In FIG. 11, the tibial alignment instrument 70 is shown with the pin 84 of the cutting block holder 77 inserted into the second wing opening 22 of the cutting block 1 to accomplish medial coupling of the tibial alignment instrument 70 with respect to the cutting block 1, and with the tab 86 inserted into the longitudinal slot 9 of the cutting block 1 to provide additional stabilization between the tibial alignment instrument 70 and the cutting block 1. By these configurations, the cutting block 1 may be coupled with the tibial alignment instrument 70 to position the cutting block 1 either centrally (FIGS. 8 and 10) laterally (FIG. 9), or medially (FIG. 11) relative to the tibia 200. The tab 86, when inserted into the longitudinal slot 9 of the cutting block 1, also prevents rotation of the cutting block 1 about the pin 84. It should be understood that other placements of the openings 20, 21 and 22 and the resultant positionings of the cutting block 1 relative to the tibial alignment instrument 70 are also contemplated.

In some embodiments, a cutting block may be coupled or attached to a tibia with one or more fasteners prior to the proximal cutting of the tibia. For example, in the illustrated embodiment shown in FIG. 12, fasteners 50 are placed through holes in the cutting block 1 to couple or attach the cutting block 1 to the tibia 200. The fasteners 50 may be placed through any combination of the base holes 10, the negative adjustment holes 8, the positive adjustment holes 12, and the skewed holes 14. In some embodiments, the fasteners 50 may be headless or smooth fasteners that have been initially/provisionally placed through the base holes 10. If an adjustment in a distal or proximal direction is determined to be necessary, the cutting block 1 may removed from the fasteners and adjusted distally or proximally by placing the cutting block 1 over the negative adjustment holes 8 or the positive adjustment holes 12. Fasteners may also be placed through the skewed holes 14 to achieve coupling between the cutting block 1 to the femur 100 when no additional adjustment is anticipated, or if the surgeon is willing to remove fasteners to accomplish further adjustments.

Figure 12:
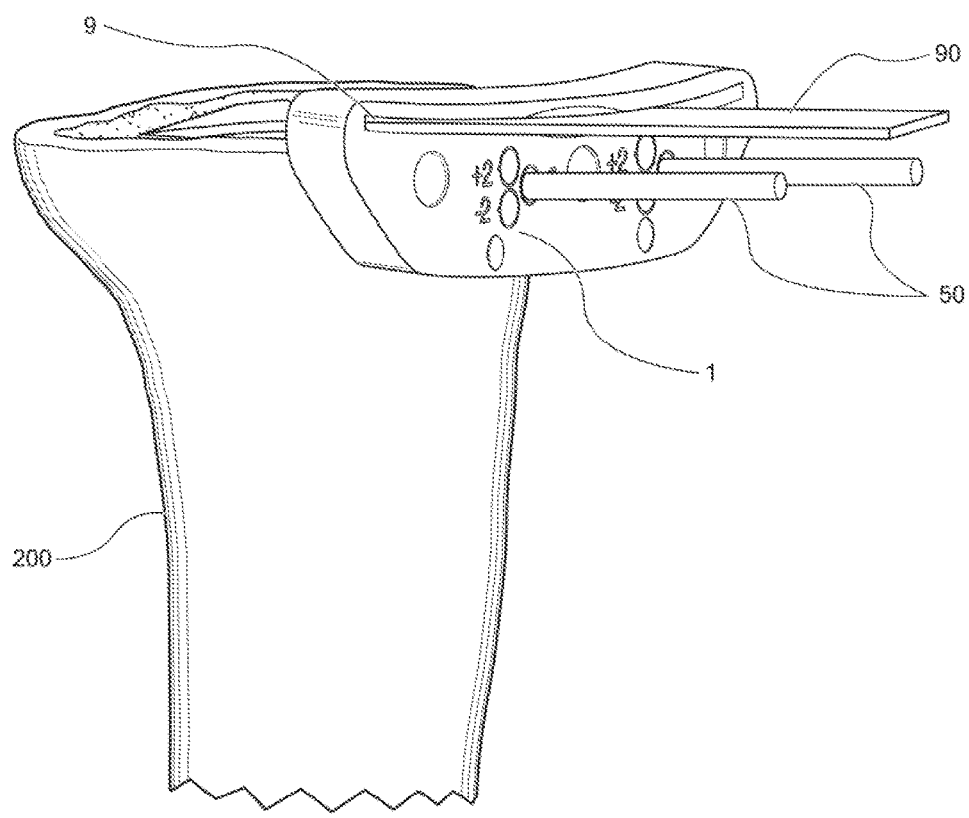
FIG. 12 is a perspective view of the cutting block of FIGS. 1-6 and 8-11 and a cutting instrument used to make a proximal tibial cut.

Method embodiments may also include forming a proximal cut to a tibia. For example and without limitation, formation of a proximal cut is shown in FIG. 12 which is formed via an end-saw 90 passing through the slot 9 in the cutting block 1. However, other suitable and effective types of saws, blades, burrs, or cutting devices may be used to accomplish cutting of a distal femur.

Figure 13:
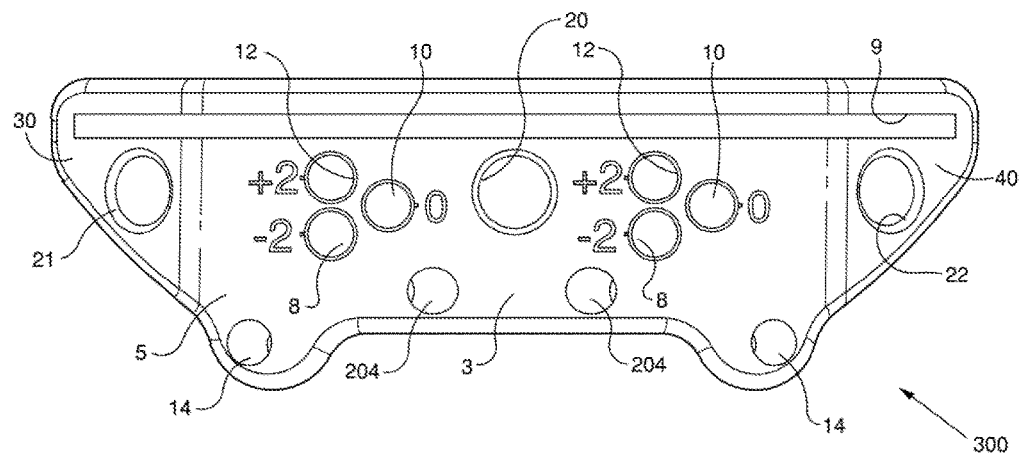
FIG. 13 is a front elevation view of another embodiment of a cutting block.
Figure 14:
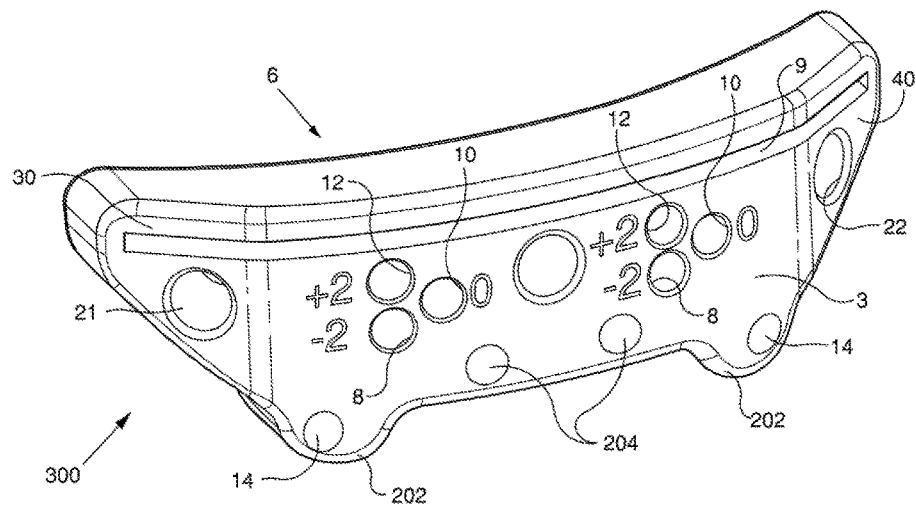
FIG. 14 is a perspective view of the cutting block of FIG. 13.

Another embodiment of a cutting block 300 is illustrated in FIGS. 13 and 14. This cutting block 300 is configured very similar to the cutting block 1 illustrated in FIGS. 1 and 2. The reference numerals of FIGS. 1 and 2 are repeated for like features of the cutting block 300. However, the cutting block 300 is shown with a slightly different overall shape having two protuberances or projections 202 (FIG. 14) extending downwardly from a lower surface of the cutting block 300. These protuberances 202 define the skewed holes 14 having axes that are arranged non-parallel with one another. In the illustrated embodiment, the two skewed holes 14 are angled such that their axes are directed towards the center of the cutting block 300. The skewed holes 14 may provide an advantage in some embodiments of more positively coupling the cutting block 300 to a femur or a tibia because the non-parallel axes prevent sliding of the cutting block 300 in a common direction along two or more fasteners placed in the non-parallel holes. Additionally, the cutting block 300 has secondary skewed holes 204 having axes that are also arranged non-parallel with one another. The skewed holes 204 have axes that are angled away from the center of the cutting block 300. The secondary skewed holes 204 can be used in combination with the skewed holes 14, or can be used alternatively relative to the skewed holes 14 to more solidly/firmly affix or attach the cutting block 300 to the tibia 200 or femur 100.

Figure 15:
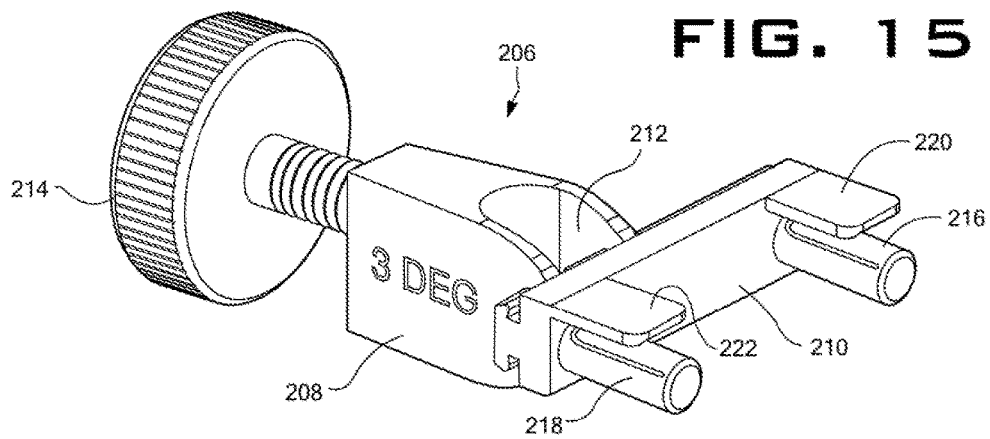
FIG. 15 is a perspective view of a cut block slide connector according to one embodiment for use with a tibial alignment instrument.
Figures 16, 17:
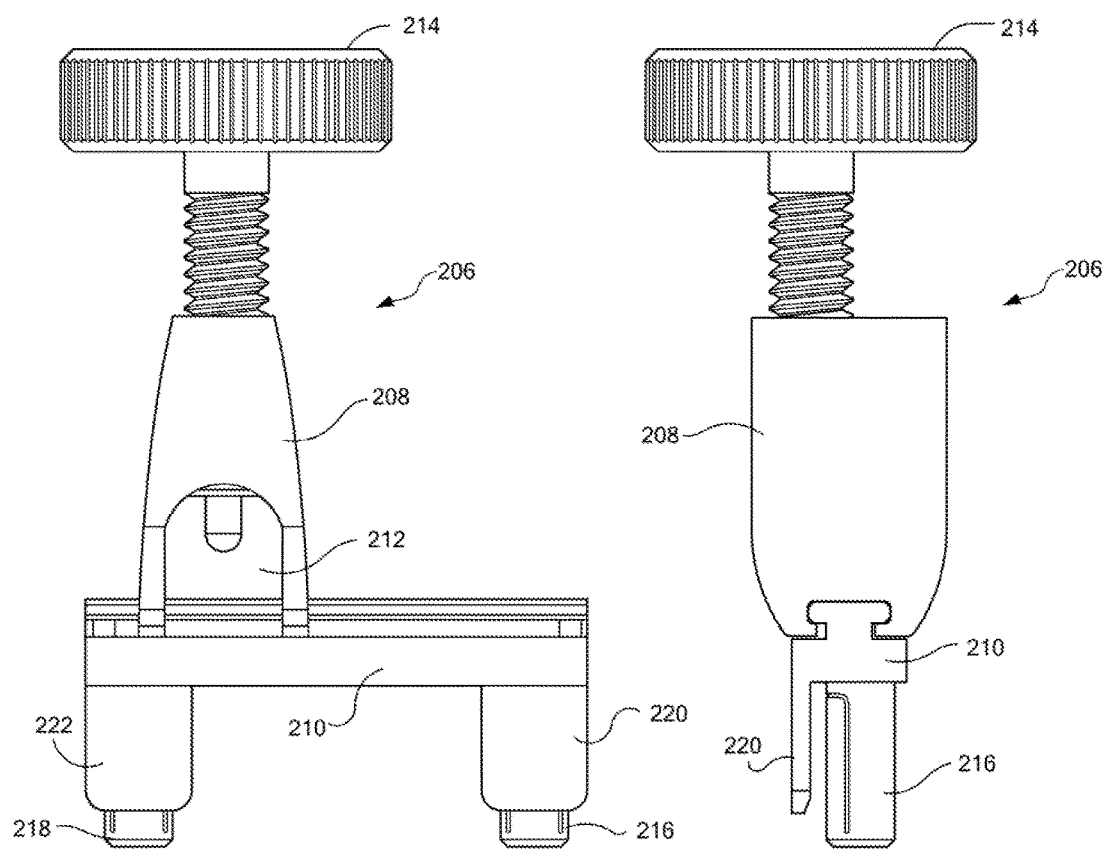
FIG. 16 is a top plan view of the cut block slide connector of FIG. 15.
FIG. 17 is a side elevation view of the cut block slide connector of FIG. 15.
Figure 18:
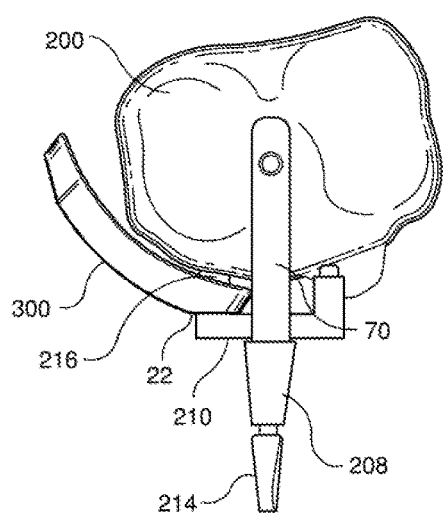
FIG. 18 is a plan view of a tibial alignment instrument similar to that shown in FIG. 8, the cutting block of FIG. 13, and utilizing the cut block slide connector of FIG. 15 with the cutting block positioned medially relative to the tibia.
Figure 19:
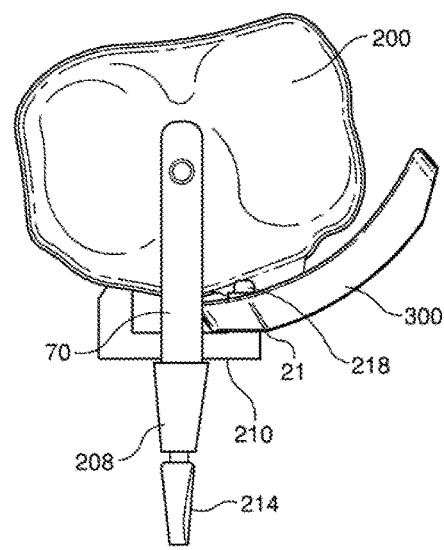
FIG. 19 is a plan view of a tibial alignment instrument similar to that shown in FIG. 8, the cutting block of FIG. 13, and utilizing the cut block slide connector of FIG. 15 with the cutting block positioned laterally relative to the tibia.

One embodiment of a cut block slide connector 206 is shown in FIGS. 15-19. The cut block slide connector 206 may be used in place of the cutting block holder 77 discussed in relation to FIGS. 7-11. The cut block slide connector 206 is generally provided with a body 208 and a sliding cutting block holder 210. The body 208 and sliding cutting block holder 210 are positioned in sliding engagement such that the cutting block holder 210 is allowed to slide either medially or laterally relative to the body 208. In the illustrated embodiment, the sliding cutting block holder 210 is angled three degrees downwardly relative to the body 208, as shown in FIG. 15. This angled arrangement is denoted by the "3 DEG" marking/indicia on the side of the body 208. The three degree angle allows the cutting block 300 to be held in a manner to allow the tibial cut to be angled downwardly three degrees from the anterior side of the tibia 200 to the posterior side of the tibia 200. In other words, the tibia 200 will be cut such that its anterior side will be slightly higher than the posterior side. The body 208 is also provided with an aperture 212 that can be received about the tibial alignment instrument 70 of FIG. 8. A thumb screw 214 is provided on the body 208 to allow the cut block slide connector 206 to be affixed to the tibial alignment instrument 70, much like the cutting block holder 77 shown in FIG. 8. The sliding cutting block holder 210 is provided with medial and lateral pins 216 and 218 which can be inserted into the cutting block 300. The cutting block holder 210 may also be provided with a pair of generally flat tabs 220 and 222 corresponding to the medial and lateral pins 216 and 218, respectively. The tabs 220 and 222 can be received in the cutting slot 9 to further stabilize the cut block slide connector 206 relative to the cutting block. 300, as shown in FIGS. 18 and 19. The body 208 and the sliding cutting block holder 210 are selectively locked or coupled together once the thumb screw 214 is tightened against the tibial alignment instrument 70.

In FIGS. 18 and 19, the cutting block 300 is shown coupled to a tibial alignment instrument. In FIG. 18, the tibial alignment instrument is shown with the cut block slide connector 206 with its medial pin 216 inserted into the body opening 22 (FIGS. 13 and 14) of the cutting block 300 to accomplish a coupling. The tab 220 is inserted into the slot 9 of the cutting block 300. Before the thumb screw 214 is fully tightened, the sliding cutting block holder 210 is allowed to move either medially or laterally to allow the cutting block 300 to be positioned in a closely approximated position with respect to the tibia 200. In FIG. 19, the tibial alignment instrument 70 is shown with the cut block slide connector 206 with its lateral pin 218 inserted into the body opening 21 (FIGS. 13 and 14) of the cutting block 300 to accomplish a coupling therebetween. Before the thumb screw 214 is fully tightened, the sliding cutting block holder 210 is allowed to move either medially or laterally to allow the cutting block 300 to be positioned in a closely approximated position with respect to the tibia 200. By this configuration, the cutting block 300 may be coupled with the tibial alignment instrument to position the cutting block 300 either medially (FIG. 18) or laterally (FIG. 19) relative to the tibia 200. The tabs 220 and 222, when inserted into slot 9 of the cutting block 300, prevent rotation of the cutting block 300 about either of the medial or lateral pins 216 and 218. However, other placements of the openings and the resultant positionings are also contemplated. As illustrated in FIGS. 18 and 19, a back 6 of the body 3 of the cutting block 300 is directed towards the anterior portion of the tibia 200. However, in other embodiments, a front or other portion of a cutting block may be directed toward a tibia designated to be cut.

Various embodiments of an instrument set, in whole or its components individually, may be made from any suitable biocompatible material. For example and without limitation, biocompatible materials may include in whole or in part: non-reinforced polymers, reinforced polymers, metals, ceramics, adhesives, reinforced adhesives, and combinations of these materials. Reinforcing of polymers may be accomplished with carbon, metal, or glass or any other effective material. Examples of biocompatible polymer materials include polyamide base resins, polyethylene, low density polyethylene, polymethylmethacrylate (PMMA), polyetheretherketone (PEEK), polyetherketoneketone (PEKK), a polymeric hydroxyethylmethacrylate (PHEMA), and polyurethane, any of which may be reinforced. Example biocompatible metals include stainless steel and other steel alloys, cobalt chrome alloys, zirconium, oxidized zirconium, tantalum, titanium, titanium alloys, titanium-nickel alloys such as Nitinol and other superelastic or shape-memory metal alloys.

Terms such as anterior, posterior, medial, lateral, central, top, bottom, front, back, and the like are used as relative terms herein. However, such terms are not limited to specific coordinate orientations, distances or sizes, but are instead used to describe relative positions referencing particular embodiments. Such terms are not generally limiting to the scope of the claims made herein. Any embodiment or feature of any section, portion, or any other component shown or particularly described in relation to various embodiments of similar sections, portions or components set forth herein may be interchangeably applied, to any other similar embodiment or feature shown or described herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. A cutting block configured to guide cutting of a tibia and a femur in preparation for one or more knee arthroplasty implants, the cutting block comprising:
    a body including:
        a front,
        a back, and
        one or more holes extending through the body for receipt of fasteners to couple the body with the tibia or the femur;
    a first wing adjacent to the body; and
    a second wing adjacent to the body and positioned opposite the first wing;
    wherein the body, the first wing, and the second wing include substantially similar openings configured to couple with a tibial alignment instrument such that the cutting block may be coupled with the tibial alignment instrument to position the cutting block medially, laterally, or centrally relative to the tibia.

2. The cutting block of claim 1, wherein the cutting block is generally curved such that a generally convex side defines the front of the body and a generally concave side defines the back of the body.

3. The cutting block of claim 2, wherein the body is generally curved such that the generally convex side is on the front and the generally concave side is on the back.

4. The cutting block of claim 1, wherein the one or more holes include at least two holes arranged along axes that are parallel to one another.

5. The cutting block of claim 1, wherein the one or more holes include at least two holes arranged along axes that are not parallel to one another.

6. The cutting block of claim 1, wherein the front of the body includes markings indicating adjustments that may be made to a position of the cutting block relative to the tibia or the femur by removing the cutting block from one or more fasteners positioned in a set of the one or more holes in the cutting block and placing the cutting block over the one or more fasteners in a different set of the one or more holes in the cutting block.

7. The cutting block of claim 1, wherein the back of the body includes markings indicating adjustments that may be made to a position of the cutting block relative to the tibia or the femur by removing the cutting block from one or more fasteners positioned in a set of one or more holes in the cutting block and placing the cutting block over the one or more fasteners in a different set of the one or more holes in the cutting block.

8. The cutting block of claim 1, wherein the first wing extends along a major axis that is not arranged parallel with a major axis of the body.

9. The cutting block of claim 1, wherein the second wing extends along a major axis that is not parallel with a major axis of the body.

10. The cutting block of claim 1, wherein at least two of the substantially similar openings that are configured to couple with a tibial alignment instrument are arranged along converging axes such that coupling the cutting block through the at least two of the substantially similar openings while maintaining the tibial alignment instrument in a constant position relative to the tibia rotates the cutting block relative to the tibia.

11. The cutting block of claim 1, wherein the substantially similar openings in the body, the first wing, and the second wing that are configured to couple with a tibial alignment instrument are arranged along converging axes such that coupling the cutting block through the openings while maintaining the tibial alignment instrument in a constant position relative to the tibia rotates the cutting block relative to the tibia.

12. An instrument set configured to guide cutting of a tibia and a femur in preparation for one or more knee arthroplasty implants, comprising:
    a femoral alignment instrument;
    a tibial alignment instrument; and
    a cutting block configured to couple with the femoral alignment instrument and the tibial alignment instrument, the cutting block comprising:
        a body including:
            a front,
            a back, and
            one or more holes extending through the body for receipt of fasteners to couple the body with the tibia or the femur;
        a first wing adjacent to the body, and
        a second wing adjacent to the body and positioned opposite from the first wing;
        wherein the body, the first wing, and the second wing include substantially similar openings configured to couple with the tibial alignment instrument such that the cutting block may be coupled with the tibial alignment instrument to position the cutting block medially, laterally, or centrally relative to the tibia; and
        wherein at least one of the substantially similar openings in the body configured to couple with the tibial alignment instrument is also configured to couple with the femoral alignment instrument.

13. The instrument set of claim 12, wherein the femoral alignment instrument includes an intramedullary portion configured to be inserted into an intramedullary canal of the femur.

14. The instrument set of claim 12, wherein the tibial alignment instrument does not include an intramedullary portion configured to be inserted into an intramedullary canal of the tibia.

15. The instrument set of claim 12, wherein the cutting block is generally curved such that a generally convex side includes the front of the body and a generally concave side includes the back of the body.

16. The instrument set of claim 12, wherein the body is generally curved such that a generally convex side extends along the front of the body and a generally concave side extends along the back of the body.

17. The instrument set of claim 12, wherein the one or more holes include at least two holes arranged along axes that are parallel to one another.

18. The instrument set of claim 12, wherein the one or more holes include at least two holes arranged along axes that are not parallel to one another.

19. The instrument set of claim 12, wherein the front of the body includes markings indicating adjustments that may be made to a position of the cutting block relative to the tibia or the femur by removing the cutting block from one or more fasteners positioned in a set of the one or more holes in the cutting block and placing the cutting block over the one or more fasteners in a different set of the one or more holes in the cutting block.

20. The instrument set of claim 12, wherein the back of the body includes markings indicating adjustments that may be made to a position of the cutting block relative to the tibia or the femur by removing the cutting block from one or more fasteners positioned in a set of the one or more holes in the cutting block and placing the cutting block over the one or more fasteners in a different set of the one or more holes in the cutting block.

21. The instrument set of claim 12, wherein the first wing extends along a major axis that is not parallel with a major axis of the body.

22. The instrument set of claim 12, wherein the second wing extends along a major axis that is not parallel with a major axis of the body.

23. The instrument set of claim 12, wherein at least two of the substantially similar openings in the body, the first wing, and the second wing that are configured to couple with a tibial alignment instrument are arranged along converging axes such that coupling the cutting block through the at least two of the substantially similar openings while maintaining the tibial alignment instrument in a constant position relative to the tibia rotates the cutting block relative to the tibia.

24. The instrument set of claim 12, wherein the substantially similar openings in the body, the first wing, and the second wing that are configured to couple with a tibial alignment instrument arranged along converging axes such that coupling the cutting block through different openings while maintaining the tibial alignment instrument in a constant position relative to the tibia rotates the cutting block relative to the tibia.

25. A method of preparing a tibia and a femur to receive one or more knee arthroplasty implants, the method comprising:
providing a cutting block configured to guide cutting of a distal femur and to guide cutting of a proximal tibia;
aligning a femoral alignment instrument with the femur to enable formation of a distal cut of the femur;
coupling the cutting block to the femoral alignment instrument;
making the distal cut of the femur;
aligning a tibial alignment instrument with the tibia to enable formation of a proximal cut of the tibia;
coupling the cutting block to the tibial alignment instrument at one of three different openings in the cutting block wherein the three different openings are provided as substantially similar openings configured to couple with the tibial alignment instrument such that the cutting block may be coupled with the tibial alignment instrument to position the cutting block medially, laterally, or centrally relative to the tibia; and
making the proximal cut of the tibia.

26. The method of claim 25, wherein the coupling of the cutting block to the femoral alignment instrument includes coupling the cutting block to the femoral alignment instrument such that a front of the cutting block is directed toward the femur.

27. The method of claim 25, further comprising coupling the cutting block to the femur with one or more fasteners prior to making the distal cut of the femur.

28. The method of claim 25, wherein the coupling of the cutting block to the tibial alignment instrument includes coupling the cutting block to the tibial alignment instrument such that a back of the cutting block is directed toward the tibia.

29. The method of claim 25, further comprising coupling the cutting block to the tibia with one or more fasteners prior to making the proximal cut of the tibia.

30. The cutting block of claim 1, wherein the first wing includes a first of the openings, the second wing includes a second of the openings, and the body includes a third of the openings.

31. The instrument set of claim 12, wherein the first wing includes a first of the openings, the second wing includes a second of the openings, and the body includes a third of the openings.

32. The instrument set of claim 31, wherein the instrument set has a first configuration in which the cutting block is coupled with the tibial alignment instrument via the first of the openings such that the cutting block is positioned medially relative to the tibia;
wherein the instrument set has a second configuration in which the cutting block is coupled with the tibial alignment instrument via the second of the openings such that the cutting block is positioned laterally relative to the tibia; and
wherein the instrument set has a third configuration in which the cutting block is coupled with the tibial alignment instrument via the third of the openings such that the cutting block is positioned centrally relative to the tibia.

33. The instrument set of claim 32, wherein the instrument set has a fourth configuration in which the cutting block is coupled with the femoral alignment instrument such that the cutting block is operable to guide formation of a distal resection cut in a femur; and
wherein with the instrument set in each of the first configuration, the second configuration, and the third configuration, the cutting block is operable to guide formation of a proximal resection cut in the tibia.

* * * * *